US006845216B2

(12) United States Patent
Schuster et al.

(10) Patent No.: US 6,845,216 B2
(45) Date of Patent: Jan. 18, 2005

(54) TEMPERATURE CONTROLLING DEVICE FOR AEROSOL DRUG DELIVERY

(75) Inventors: Jeffrey A. Schuster, Oakland, CA (US); Christopher J. Flaim, Modesto, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

(21) Appl. No.: 10/618,064

(22) Filed: Jul. 11, 2003

(65) Prior Publication Data

US 2004/0105665 A1 Jun. 3, 2004

Related U.S. Application Data

(63) Continuation of application No. 09/839,248, filed on Apr. 20, 2001, now Pat. No. 6,629,526, which is a continuation of application No. 09/690,242, filed on Oct. 16, 2000, now Pat. No. 6,263,872, which is a continuation of application No. 09/107,306, filed on Jun. 30, 1998, now Pat. No. 6,131,570, which is a continuation-in-part of application No. 08/752,946, filed on Nov. 21, 1996, now Pat. No. 5,906,202.

(51) Int. Cl.[7] .......................... F24E 6/00; A61M 15/00
(52) U.S. Cl. .................................. 392/390; 128/200.11
(58) Field of Search ................................ 392/386, 387, 392/390, 394, 396, 397, 402, 403; 128/200.11, 200.14, 200.19, 201.13, 203.12, 203.16, 203.17, 203.26, 203.27

(56) References Cited

U.S. PATENT DOCUMENTS

| | | | | |
|---|---|---|---|---|
| 3,872,280 A | * | 3/1975 | Van Dalen | |
| 3,933,276 A | | 1/1976 | Packham et al. | |
| 3,949,743 A | * | 4/1976 | Shanbrom | |
| 4,106,503 A | * | 8/1978 | Rosenthal et al. | |
| 4,365,141 A | * | 12/1982 | Weiss | 392/385 |
| 4,523,589 A | * | 6/1985 | Krauser | 128/203.27 |
| 4,587,966 A | | 5/1986 | Albarda | |
| 4,653,494 A | | 3/1987 | Ruderian | |
| 4,682,010 A | * | 7/1987 | Drapean et al. | |
| 4,733,059 A | * | 3/1988 | Goss et al. | 219/548 |
| 4,735,217 A | * | 4/1988 | Gerth et al. | |
| 4,911,157 A | * | 3/1990 | Miller | |
| 4,922,901 A | | 5/1990 | Brooks et al. | |
| 4,947,875 A | | 8/1990 | Brooks et al. | |
| 5,038,769 A | | 8/1991 | Krauser | |
| 5,246,018 A | * | 9/1993 | Deevi et al. | |
| 5,249,586 A | * | 10/1993 | Morgan et al. | |
| 5,388,574 A | * | 2/1995 | Ingebrethsen | 128/203.17 |
| 5,497,763 A | | 3/1996 | Lloyd et al. | |
| 5,522,385 A | | 6/1996 | Lloyd et al. | |
| 5,537,996 A | * | 7/1996 | McPhee | 128/204.17 |

(List continued on next page.)

OTHER PUBLICATIONS

Bates, David V., et al., (1966) "Deposition and Retention Models for Internal Dosimetry of the Human Respiratory Tract", *Health Physics*, vol. 12:173–207.

Byron, Peter R., (1986) "Prediction of Drug Residence Times in Regions of the Human Respiratory Tract Following Aerosol Inhalation", *J. of Pharm. Sciences*, vol. 75(5):433–438.

Farr, Stephen J., et al., (1996) "AERx–Development of a Novel Liquid Aerosol Delivery System Concept to Clinic", *Respiratory Drug Delivery V*, pp. 175–185.

(List continued on next page.)

*Primary Examiner*—Sang Paik
(74) *Attorney, Agent, or Firm*—Karl Bozicevic; Bozicevic, Field & Francis LLP

(57) ABSTRACT

A portable air temperature controlling device useful for warming air surrounding an aerosolized drug formulation is described. Warming the air of an aerosol makes it possible to reduce the size of aerosol particles produced by an aerosol generation device. Additionally, warming the air forces the size of the aerosol particles to be in the range required for systemic drug delivery independent of ambient conditions. Smaller particles can be more precisely targeted to different areas of the respiratory tract.

12 Claims, 4 Drawing Sheets

U.S. PATENT DOCUMENTS

| | | |
|---|---|---|
| 5,660,166 A | 8/1997 | Lloyd et al. |
| 5,665,262 A | 9/1997 | Hajaligol et al. |
| 5,672,581 A | 9/1997 | Rubsamen et al. |
| 5,709,202 A | 1/1998 | Lloyd et al. |
| 5,718,222 A | 2/1998 | Lloyd et al. |

OTHER PUBLICATIONS

Ferron et al. (1988) "Inhalation of Salt Aerosol Particles—II. Growth and Deposition in the Human Respiratory Tract." *J. Aerosol Sci.*, vol. 19(5):611–631.

Hickey, A.J., et al., (1990) "Effect of Hydrophobic Coating on the Behavior of a Hygroscopic Aerosol Powder in an Environment of Controlled Temperature and Relative Humidity", *J. of Pharm. Sciences*, vol. 79(11):1009–1014.

Morrow et al. (1966) "Deposition and retention models for internal dosimetry of the human respiratory tract. Task group on lung dynamics," *Health Phys.*, vol. 12(2):173–207.

Phipps, Paul R., et al., (1990) "Droplets Produced by Medical Nebulizers: Some Factors Affecting Their Size and Solute Concentration" *Chest*, vol. 97:1327–1332.

Stahlhofen et al. (1980) "Experimental determination of the regional deposition of aerosol particles in the human respiratory tract." *Am Ind Hyg Assoc J*; vol. 41(6):385–98a.

\* cited by examiner

TEMPERATURE CONTROLLING DEVICE FOR AEROSOL DRUG DELIVERY

CROSS REFERENCES

This application is a continuation of U.S. application Ser. No. 09/839,248 filed Apr. 20, 2001 U.S. Pat. No. 6,629,526 which is a continuation of U.S. application Ser. No. 09/690,242 filed Oct. 16, 2000 (now U.S. Pat. No. 6.263,872, issued Jul. 24, 2001, which is a continuation of U.S. application Ser. No. 09/107,306 filed Jun. 30, 1998 (now U.S. Pat. No. 6,131,570, issued Oct. 17, 2000) which is a continuation-in-part of U.S. application Ser. No. 08/752,2946 filed Nov. 21, 1996 (now U.S. Pat. No. 5,906,202 issued May 25, 1999) which applications and patents are incorporated herein by reference and to which applications we claim priority under 35 U.S.C. §120.

FIELD OF THE INVENTION

This invention relates generally to portable devices and methods useful for optimizing the size distribution of a medical aerosol, and reducing the amount of variability arising from variations in ambient conditions. More specifically, this invention relates to battery powered, portable devices for controlling the temperature of air surrounding aerosol particles of drugs and delivering the drug to a specific area of the lung.

BACKGROUND OF THE INVENTION

There are several known methods for the aerosolized delivery of drugs. In general, the methods include: (1) placing an aqueous formulation within a nebulizer device which by various mechanical means causes the drug formulation to be aerosolized in a continuous stream which is inhaled by the patient; (2) dry powder inhalers which create a fine powder of the drug and aerosolize the powder in a dust form which is inhaled; (3) metered dose inhalers which dissolve or disperse the drug in a low boiling point propellant; and (4) more current devices such as that disclosed within U.S. Pat. No. 5,660,166 issued Aug. 26, 1997 which force aqueous formulations through a nozzle to create an aerosol which is inhaled by the patient.

In accordance with each of the known methods for aerosolizing a drug it is important to produce an aerosol which has particles within a desired size range, e.g. 0.5 to 12.0 microns and more preferably 1.0 to 3.5 microns. In addition to producing small particles it is preferable to produce particles which are relatively consistent in size, i.e. produce an aerosol wherein a large percentage of the particles fall within the desired size range. In addition, it is desirable to produce an aerosol which has the property that the key measures of aerosol quality, such as particle size and dose emitted are not effected by ambient conditions such as temperature and or relative humidity. With any of the known methods for aerosol delivery of drugs there are difficulties with respect to making the particles sufficiently small. Along with these difficulties there are difficulties with respect to creating particles which are relatively consistent in size. These difficulties are particularly acute when attempting to provide For systemic delivery of an aerosolized drug. Efficient systemic delivery requires that the aerosol be delivered deeply into the lung so that the drug can efficiently reach the air/blood exchange membranes in the lung and migrate into the circulatory system.

Aerosol delivery to the lungs has been used for delivery of medication for local therapy (Graeser and Rowe, *Journal of Allergy* 6:415 1935). The large surface area, thin epithelial layer, and highly vascularized nature of the peripheral lung (Taylor, *Adv. Drug Deliv. Rev.* 5:37 1990) also make it an attractive site for non-invasive systemic delivery. Unlike other avenues of non-invasive delivery such as trans-dermal, nasal, or buccal, the lung is designed as a portal of entry to the systemic circulation. However, targeting the peripheral lung requires careful control of the aerosol particle size and velocity distributions, in order to by pass the exquisitely evolved particle filtering and clearing functions of the bronchial airways.

Many authors have reported results of experiments or mathematical models showing that micron sized particles are required for delivery to the lungs (c.f. Stahlhofen, Gebhart and Heyder, *Am. Ind. Hyg. Assoc. J.* 41:385 1980, or Ferron, Kreyling and Haider, *J. Aerosol Sci.* 19:611 1987). One example is the model of the Task Group on Lung Dynamics (Morrow et. al. *Health Physics* 12:173 1966). As FIG. 1 shows, under the assumptions of this model, particles of diameter less than ~3.5 $\mu$m are required to avoid the oropharynx and bronchial airways. FIG. 1 might suggest that the maximum efficiency of deposition of drugs delivered to the pulmonary region of the lung is limited to ~60%. However, as can be seen in FIG. 2, efficiencies approaching 100% can be achieved by allowing the particles to settle gravitationally during a ten second breath hold (Byron, *J. Pharm. Sci.* 75:433 1986).

It has been demonstrated that ambient conditions can strongly effect the amount of aerosol particles less than 3.5 $\mu$m emitted from aerosol generation device. One example is the work of Phipps and Gonda (*Chest* 97:1327–1332, 1990) showing that the amount of aerosol less than 3.5 $\mu$m delivered by a aerosol drug delivery device changed from 33% to 73% when the relative humidity changed from 100% to 70%. Similar work with a dry powder (Hickey et al *J. Pharm. Sci.* 79, 1009–1011) demonstrated a chance in the amount of aerosol less than 3.5 $\mu$m from 9% to 42% when the ambient relative humidity changed from 97% to 20%. These data are tabulated in Table 1.

TABLE 1

Effect of RH on Particle Size Distribution

| Aerosol | T, °C. | R. H., % | % <3.5 $\mu$m |
|---|---|---|---|
| Isotonic Saline[1], Hudson Up-Draft | 23–24° | 100% | 33% |
| Isotonic Saline[1], Hudson Up-Draft | 23–24° | 65–75% | 73% |
| Fluorescein Powder[2] | 37 ± 0.1° | 97 ± 1% | 9% |
| Fluorescein Powder[2] | 37 ± 0.1° | 20 ± 5% | 42% |

[1]Phipps and Gonda, 1990
[2]Hickey et al 1990

Many pharmaceutical compounds of a wide range of molecular weights are potential candidates for systemic delivery via the lung. Small molecules analgesics such as morphine or fentanyl could be delivered to pain patients, e.g. cancer or post-operative patients. Morphine has demonstrated bioavailability when delivered via the lung (S. J. Farr, J. A. Schuster, P. M. Lloyd, L. J. Lloyd, J. K. Okikawa, and R. M. Rubsamen. In R. N. Dalby, P. R. Byron, and S. J. Farr (eds.), *Respiratory Drug Deliver V.* Interpharm Press, Inc., Buffalo Grove, 1996, 175–185).

Potent peptide hormones are available for a variety of therapeutic indications. Leuprolide, for example, is a GNRH super-agonist useful in the treatment of endometriosis and prostate cancer. Leuprolide also has potential applications in the field of breast cancer management and the treatment of precocious puberty. Calcitonin enhances metabolism and may be a useful therapeutic agent for the management of osteoporosis, a common complication of aging.

To treat conditions or diseases of the endocrine system, pharmaceutical formulations containing potent peptide hormones are typically administered by injection. Because the stomach presents a highly acidic environment, oral preparations of peptides are unstable and readily hydrolyzed in the gastric environment. Currently, there are no oral preparations of therapeutic peptide agents commercially available.

Both calcitonin and leuprolide can be administered nasally. (See Rizzato et al., *Curr. Ther. Res.* 45:761–766, 1989.) Both drugs achieve blood levels when introduced into the nose from an aerosol spray device. However, experiments by Adjei et al. have shown that the bioavailability of leuprolide when administered intranasally is relatively low. However, an increase in the bioavailability of leuprolide can be obtained by administering the drug into the lung. Intrapulmonary administration of leuprolide has been shown to be an effective means of non-invasive administration of this drug (Adjei and Garren, *Pharmaceutical Research*, Vol. 7, No. 6, 1990).

Intrapulmonary administration of drugs has the advantage of utilizing the large surface area available for drug absorption presented by lung tissue. This large surface area means that a relatively small amount of drug comes into contact with each square centimeter of lung parenchyma. This fact reduces the potential for tissue irritation by the drug and drug formulation. Local irritation has been seen with nasal delivery of insulin and has been a problem for commercialization of nasal preparations of that drug. It is a problem with peptide hormones that they are very potent with effects that are not immediately manifested. For example, therapy with leuprolide for prostate cancer does not typically produce any acute clinical effects. Similarly, prophylaxis against osteoporosis with calcitonin will not produce any acute symptoms discernible to the patient. Therefore, administration of each dose of these drugs must be reliable and reproducible.

SUMMARY OF THE INVENTION

A portable, self-contained device useful for controlling the temperature of the air surrounding an aerosolized drug formulation is provided. The temperature controlling device is comprised of a heating element (preferably in the form of a wire coil) which warms the air surrounding an aerosolized pharmaceutical formulation. The warming of the air results in evaporating liquid carrier from aerosol particles of a liquid formulation, thereby obtaining a smaller, more uniform particle size. Alternatively, or in addition, the warming of the air can prevent or impede the accumulation of water (which might condense from the air) on particles of a liquid formulation or especially a dry powder. Because warming of ambient air will always result in a reduced relative humidity, it is possible to ensure that only evaporation will occur, as differentiated from introducing aerosols into uncontrolled ambient air, where growth (i.e., condensation of water vapor on an aerosolized particle) or evaporation are generally possible. Thus the use of a temperature controller can reduce the dependence of particle size on ambient conditions. The results of such make it possible to more precisely target areas of the respiratory tract by adjusting particle size by warming the air.

To have practical utility any temperature controller to be used by patients administering inhaled drugs must be small, efficient, and highly portable. The invention preferably comprises a portable power source such as a battery (e.g. 10 AA or similarly sized batteries or less), a control circuit, a temperature sensing means, a relay, and a heating element. These components are preferably combined with an aerosol generating means which is most preferably the type which moves formulation through holes. The air surrounding the aerosol particles is preferably warmed to the extent that 50% or more of the carrier is evaporated away from the particles of an aqueous formulation. More preferably, the warming results in providing particles which are substantially dry— all free water being evaporated away. A very important aspect of the invention is in a temperature controller which achieves the desired effects while being powered only by a battery.

The heating element is preferably in the form of a wire coil of an alloy containing some or all of: nickel, chromium, copper, and iron and having a weight of about 5 grams (±4 grams) and a gauge of about 26 (±10 gauge). Alternatively, the heating element may be in the form of a stamped and/or folded metal sheet. Different types of heating elements could be used provided they meet certain criteria. It must be possible to heat the element with a portable battery source in a short period of time, e.g. one minute or less. The element is preferably capable of storing sufficient energy to warm the air (e.g. 0.5 to 4 liters or more of air) surrounding the aerosol particles sufficiently to evaporate all or most of the carrier, even at high ambient relative humidity. The element must also be capable of quickly releasing heat energy to the air, e.g. releasing 20 joules or more of energy in 10 seconds or less, preferably about 2.5 seconds or less. Stated functionally, the heating element must be able to absorb and then release heat energy in amount sufficient to control particle size for a useful aerosolized dose of formulation and that energy must be absorbed and released in a period of time which is sufficiently short to be practically used during aerosolized drug delivery.

Key to the functioning of the invention is the fact that the time for a heated object to cool off is significantly shorter in moving air than in still air. Thus it is possible to preheat the element over a period of time of 10–60 seconds and store the heat for a similar period of time, and then deliver the heat into moving air in a period of time of 1–10 seconds. The heating element must be able to deliver heat back to the air in a short period, e.g. a period which correspond to the length of a patient's inhalation.

The invention increases the number and types of pharmaceutical formulations which can be administered efficiently and reproducibly by inhalation. More particularly, the invention makes it possible to inhale formulations which are intended for systemic delivery, including peptides such as insulin and analogs of insulin (e.g., insulin lispro). This is done by increasing the reproducibility of dosing by adjusting particle size to a consistent level in different surrounding humidities. Further, particular areas of the lung are targeted by (1) including aerosolized formulation in precisely determined volumes of air, (2) warming air surrounding the aerosolized formulation so as to evaporate carrier and reduce the particle size and/or to prevent water vapor in the air from condensing on particles, (3) excluding aerosolized formulation from other volumes of air delivered to the lung in order to correctly position an aerosol. Further, the heating means can be used with any type of means of generating an aerosol. More specifically, the heating means can be used with a nebulizer, a dry powder inhaler or metered dose inhaler. However, the major benefits of the invention are obtained when used with a device which creates aerosolized particles by moving liquid (aqueous or ethanolic) formulations through small holes to create particles (see U.S. Pat. No. 5,718,222 issued Feb. 17, 1998). All types of nebulizers benefit from the invention by reducing variable effects caused by the environment, e.g., changes in humidity.

The amount of energy added can be adjusted depending on factors such as the desired particle size, the amount of the carrier to be evaporated, the water vapor content (humidity) and temperature of the surrounding air, the composition of the carrier, and the region of the lung targeted.

To obtain reproducible, efficient systemic delivery it is desirable to get the aerosolized formulation deeply into the lung. This requires the delivery of the formulation in aerosol particles of diameter less than approximately 3.5 $\mu$m. Direct generation of particles in this size range can be difficult, due to the large ratio of surface area to volume of these small particles. Energy may be added in an amount sufficient to evaporate all or substantially all the carrier from an aqueous aerosol and thereby provide particles of dry powdered drug or highly concentrated drug formulation to a patient which particles are (1) uniform in size regardless of the ambient humidity and temperature (2) preferably produced from a liquid formulation, and (3) smaller due to the evaporation of the carrier.

A primary object of the invention is to provide an air temperature controlling device comprised of a receptacle for holding a self-contained power source such as electric power cells forming a battery, a channel comprising an air flow path which includes an opening into which air can be inhaled and a second opening into which air is delivered and aerosol is generated, a heating element connected to the electrical contacts of the receptacle and positioned in a manner such that air flowing by the heating element flows through the channel, wherein the device is a hand-held, self-contained device having a total weight of one kilogram or less.

It is another object of the invention to provide such a device wherein the heating element is comprised of an alloy containing copper, chromium, iron and/or nickel which heating element is preferably in the form of a wire having a gauge in the range of about 16 to 36 weighing approximately 0.5 to 10 grams.

An important advantage of the invention is that the heating device can heat a sufficient amount of air so as to evaporate a sufficient amount of carrier on aerosolized particles to make the particles consistent in size and sufficiently small as to improve the repeatability and efficiency of drug delivery.

It is an object of this invention to provide a portable air temperature controlling device able to warm the air surrounding the particles of an aerosolized drug formulation.

It is a further object of the invention to provide a drug delivery device containing such a heating element which is heated by a portable, self-contained energy source.

It is a further object of the invention to provide methods of administering aerosolized drug formulations in which the air surrounding the aerosolized formulation is warmed using a portable air temperature controlling device.

An advantage of the present invention is that it can be used for ambulatory patients.

Another object of the invention is that it makes it possible to adjust particle size by adding energy to the air surrounding the particles in an amount sufficient to evaporate carrier and reduce total particle size.

Another object or the invention is that it reduces or eliminates the variability in particle size due to variations in ambient relative humidity and temperature by ensuring that the delivered particles are in the range of 1–3.5 $\mu$m independent of ambient conditions. This object of the invention car, apply equally well to aerosol generation devices that generate aerosols of liquid solutions of drug, liquid suspensions of drug, or dry powders of drug.

Another object is to provide a device for the delivery of aerosols which measures ambient humidity via a solid state hygrometer, and/or measures ambient temperature via a temperature sensor.

A feature of the invention is that drug can be dispersed or dissolved in a liquid carrier such as water and dispersed to a patient as dry or substantially dry particles.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Figure 1:
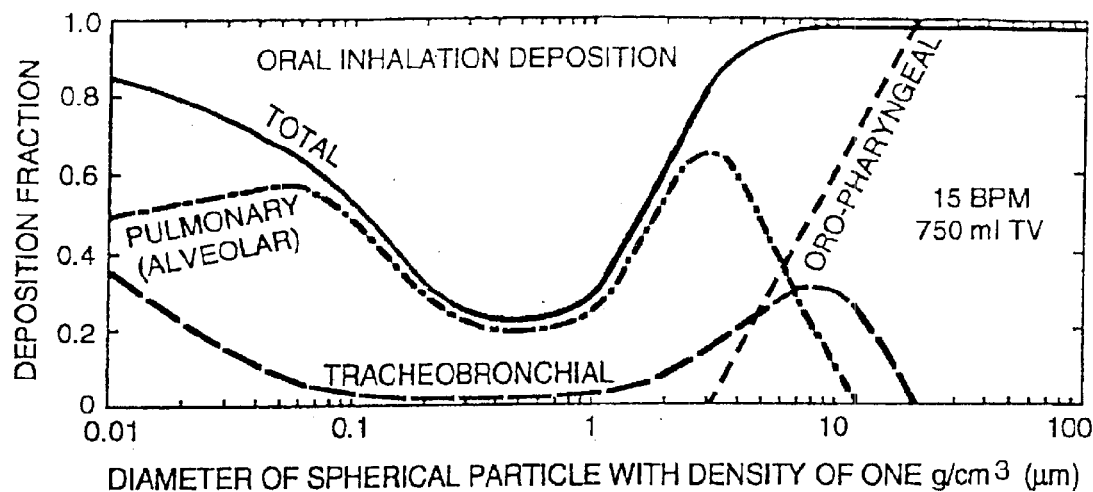
FIG. 1 is a graphic model showing the fraction of particles that deposit in the pulmonary, tracheobronchial, and oropharyngeal compartments, as a function of particle diameter.

Before the present air temperature controlling device, method of aerosolizing formulations and devices and formulations used in connection with such are described, it is to be understood that this invention is not limited to the particular embodiments described, as such heating elements, methods, devices, packages, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an aerosolized compound" includes a plurality of such compounds, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "portable air temperature controlling device", "air temperature controller" and the like refer to a self-contained device comprising a heating element which can be positioned in a aerosol delivery device in a manner such that air of an aerosol created by the device is warmed when contacting the heating element. The device preferably includes a receptacle for a power source for the heating of the heating element, and a control circuit to monitor and control the temperature of the heating element.

The term "receptacle" refers to a location in a portable drug delivery device for connecting a portable power source which power source is preferably two or more electric cells, i.e. a battery. The air temperature controlling device is preferably an integral part of a aerosol delivery device which together (with the power source) weigh less than 1.5 kg; more preferably, less than 0.75 kg. The receptacle may consist of an attachment point essentially outside of the device, or preferably an enclosed volume with a door that contains the power source inside the device. The receptacle preferably contains a method of connecting and disconnecting the means of transmitting power from the power source to the air temperature controlling device, such as electrical contacts.

The term "portable power source" refers to any source capable of generating power which can be transferred to the heating element in the portable air temperature controlling device, and preferably is a source of electrical energy, more preferably stored in a chemical cell which is an electric cell—two or more electric cells combined forms a battery. In a preferred embodiment the power source is one or more electrical cells, (i.e. a battery) which is/are sufficiently small such that when loaded into the device the device remains easily portable, e.g., AA size, C size or D size or smaller. Chemical reactions (especially the catalytic combustion of butane), hand-powered generators or friction devices could also be used.

The term "heating element" refers to any element capable of converting power provided by a portable power source into heat and releasing it to the surrounding air. In a preferred embodiment the heating element is a metal. The exact structure of the element is not critical, but it must be capable of transferring its heat to the air then to the aerosol over a period of from about 0.1 to about 10 seconds, more preferably about 1–2 seconds. In a preferred embodiment, the heating element is coiled nickel chromium or nickel copper wire, which wire is present in an amount ranging from about 1 to about 10 grams, more preferably about 2–4 grams. If the source of power is a electric cell or group of electric cells (a battery), the heating element must be designed so that its operation is consistent with a battery which is portable (size and weight are small) and can provide enough energy over a short period of time (e.g., one minute or less) to heat the heating element so that it holds enough energy to warm the air into which the aerosol is generated sufficiently to evaporate the desired amount of carrier away from the particles. For example, if the heating element is in the form of a metal wire coil, the wire can not be too thick or too thin. A nickel chromium wire of about 26±10 gauge is preferred.

The terms "hormone," "hormone drug," "pharmaceutically active hormone formulation," "peptide used in endocrine therapy," "peptide hormone drug," "peptide drug" and the like are used interchangeably herein. A hormone drug as described herein is a peptide drug which has been prepared in a pharmaceutically effective formulation and is useful in endocrine therapy. Specifically, a peptide drug of the type described herein is useful for exogenously modifying the behavior of a patient's endocrine system. Peptide drugs which are used in the present invention include those listed in Table 2, it being noted that these peptides preferably contain less than 50, more preferably less than 27, amino acids. Drug of smaller size are preferred. Particularly useful peptide drugs for use with the invention include leuprolide, calcitonin, and nafarelin. The devices and methods disclosed herein can be used in the creation of an aerosol for inhalation into the lungs using any pharmaceutically active peptide. Examples of useful peptides include:

TABLE 2

Insulin (e.g. human recombinant)
Insulin analogs (e.g. insulin lispro)
Interferon-alpha
Interferon-gamma
HPTH (human parathyroid hormone)
GCSF (granulocyte colony stimulating factor)
GMCSF (granulocyte macrophage colony stimulating factor)
Atrual natriuretic factor
Angiotensin inhibitor
Renen inhibitor
Somatomedin
FSH (follicle stimulating hormone)
Tissue growth factors (TGF's)
Endothelial growth factors
HGF (hepatocyte growth factor)
Amylin
Factor VIII
Vasopressin
IIB/IIIA peptide antagonists The invention is intended to cover such pharmaceutically active peptides, which are synthetic, naturally occurring, glycosylated, unglycosylated, pegylated forms and biologically active analogs thereof. The invention can be applied to the aerosolized delivery of insulin and insulin analogs, particularly any monomeric insulin (e.g. insulin lispro).

The terms "drug", "pharmaceutically active drug", and "active drug" and the like are used interchangeably herein to refer to any chemical compound which, when provided to a mammal, preferably a human, provides a therapeutic effect. Preferred drugs are peptide hormones, proteins such as erythropoietin, peptides and the like including insulin and insulin analogs such as insulin lispro, small molecule drugs including morphine, fentanyl, and the like, i.e. drugs which are commonly used and which are conventionally delivered by injection.

The term "treatment" is used here to cover any treatment of any disease or condition in a mammal, particularly a human, and includes:

(a) preventing the disease or condition from occurring in a subject which may be predisposed to the disease but has not yet been diagnosed as having it;

(b) inhibiting the disease or condition, i.e. arresting its development; and/or (c) relieving the disease or condition, i.e. causing regression of the disease and/or its symptoms.

The term "dosing event" shall be interpreted to mean the administration of a drug to a patient in need thereof by the intrapulmonary route of administration which event may encompass one or more releases of drug formulation from a drug dispensing device over a period of time of 15 minutes or less, preferably 10 minutes or less, and more preferably 5 minutes or less, during which period an inhalation or multiple inhalations are made by the patient and a dose of drug is released and inhaled. A dosing event shall involve the administration of drug to the patient in an amount of about 1 µg to about 10 mg. The dosing event may involve the release of from about 1 µg to about 100 mg of drug from the device.

The term "bulk flow rate" shall mean the average velocity at which air moves through a channel considering that the flow rate is at a maximum in the center of the channel and at a minimum at the inner surface of the channel.

The term "carrier" shall mean any non-active compounds present in the formulation. The carrier is preferably a liquid, flowable, pharmaceutically acceptable excipient material which the pharmaceutically active drug is suspended in or more preferably dissolved in. Useful carriers do not adversely interact with the drug or packaging and have properties which allow for the formation of aerosol particles preferably having a diameter in the range of 0.5 to 15 microns. The particles may be formed when a formulation comprising the carrier and drug is forced through pores having a diameter of 0.25 to 3.0 microns. Preferred carriers include water, ethanol and mixtures thereof. Other carriers can be used provided that they can be formulated to create a suitable aerosol and do not adversely effect the drug or human lung tissue. The term carrier includes excipient materials which are used with formulation for nebulizers, any powder inhalers and metered dose inhalers or devices of the type described in U.S. Pat. No. 5,709,202.

The term "inspiratory volume" shall mean a measured, calculated and/or determined volume of air passing a given point into the lungs of a patient assuming atmospheric pressure ±5% and a temperature in the range of 10° C. to 40° C.

The terms "formulation" and "liquid formulation" and the like are used herein to describe any pharmaceutically active drug by itself or with a pharmaceutically acceptable carrier. A formulation could be a powder, that may have previously been spray dried, lyophilized, milled, or the like, and may contain a large amount of inactive ingredients such as lactose or mannitol. The formulation is preferably in flowable liquid form having a viscosity and other characteristics such that the formulation can be aerosolized into particles which are inhaled into the lungs of a patient after the formulation is aerosolized, e.g. by being moved through a porous membrane. Such formulations are preferably solutions, e.g. aqueous solutions, ethanolic solutions, aqueous/ethanolic solutions, saline solutions, microcrystalline suspensions and colloidal suspensions. Formulations can be solutions or suspensions of drug in a low boiling point propellant or even dry powders. Dry powders tend to absorb moisture and the invention decreases the moisture content and makes it possible to deliver particles of powder which have a consistent size even when the surrounding humidity is variable.

The term "substantially dry" shall mean that particles of formulation including an amount of carrier (e.g. water or ethanol) which is comparable to (in weight) or less than the amount of drug in the particle. Preferably such particles consist essentially of only drug with no free carrier e.g., no free water, ethanol or other liquid.

The terms "aerosol," "particles," "aerosol particles," "aerosolized formulation" and the like are used interchangeably herein and shall mean particles of formulation comprised of pharmaceutically active drug and carrier which are formed for aerosol delivery, e.g. upon forcing the formulation through a nozzle which nozzle is preferably in the form of a flexible porous membrane or generated using a jet or ultrasonic nebulizer. Preferably, the particles have a size in the range of 0.5 micron to about 12 microns (more preferably 1–3.5 microns).

The terms "particle diameter" and "diameter" are used when referring to the diameter of an aerosol particle and are defined as the "aerodynamic diameter". The "aerodynamic diameter" is the physical diameter of a sphere of unit density (1 $gm/cm^3$) that has the same terminal sedimentation velocity in air under normal atmospheric conditions as the particle in question. This is pointed out in that it is difficult to accurately measure the physical diameter of small particles using current technology and because the shape may be continually changing. In addition, the deposition of aerosol particles in the bronchial airways of a human subject is described by a Stokes impaction mechanism which is characterized by a particles aerodynamic diameter. Thus, the diameter of one particle of material of a given density will be said to have the same diameter as another particle of the same material if the two particles have the same terminal sedimentation velocity in air under the same conditions.

The terms "ambient conditions," "ambient temperature," "ambient relative humidity" refer to the conditions of the air surrounding the patient and aerosol generation device, prior to this air being entrained into the device and being conditioned by the temperature controller.

The term "aerosol generation device" refers to any device for forming an aerosol for delivery to a human. These devices include but are not limited to systems that generate aerosols from liquid formulations, such as jet or ultrasonic nebulizers, spinning top generators, devices using an orifice or an array of orifices to form an aerosol (driven by a oscillation mechanism or not), and devices for the delivery of dry powder aerosols. Different types of aerosol delivery devices can utilize the temperature controller components described herein.

The term "drug delivery device" refers to a self contained portable device for the delivery of medication by way of inhalation. The drug delivery device preferably comprises a temperature controller component.

The term "temperature sensor" refers to an electrical component that has some measurable, repeatable property that can be used to determine the temperature of the component, and thus the temperature of some other substance which the sensor is in thermal contact with, such as a heating element or the surrounding air. The temperature sensor can be a thermocouple, a diode, or preferably a resistance device such as a thermistor or RTD.

The term "temperature coefficient of resistance" refers to the amount of change of the resistance of an electrical component. The temperature of a component can be measured by measuring its resistance, assuming it has a sufficiently large temperature coefficient of resistance over the range of temperatures of interest, the resistance changes monotonically, and its resistance as a function of temperature has previously been determined. The component could be a heating element, or a temperature sensor. If the component is a heating element, the preferred alloy is a nickel-iron, or similar alloy.

Device in General

An air temperature controlling device for use in conjunction with an aerosol generation device for the delivery of drugs via aerosol to the lung is disclosed. The device has a self-contained power source included (e.g. electric cells which form a battery). The drug delivery device will include a receptacle for the self-contained power source. The receptacle may hold an electrical cell or cells in the receptacle in which case the receptacle will include electrical contacts. The drug delivery device preferably comprises a channel which forms an air flow path having a first opening into which ambient air can be drawn and a second opening from which conditioned air can be delivered to the aerosol generation device, where the driving force for the air flow is preferably the patient's inhalation. The drug delivery device preferably comprises a heating element which is connected to the contacts of the receptacle for the self-contained power source. In the preferred embodiment, the power source is a battery and the contacts are electrical contacts. However, the power source may be a container of a liquid substance such as butane or propane, in which case the contacts would be a means of connecting the power source to the means of delivering the liquid to the heating element.

The heating element is positioned in a manner such that air flowing through the air flow path contacts the heating element and is warmed. In the case of a liquid formulation, the air is warmed to the extent that it can hold essentially all of the carrier in the particles after it has been cooled by the process of carrier evaporation (see FIG. 2), under all ambient conditions expected to be encountered in the lifetime of the device. In the case of a dry powder inhaler, the air is warmed to the extent that particle growth is inhibited at all ambient conditions expected to be encountered in the lifetime of the device. Preferably, the air is warmed in an amount such as to result in the evaporation of 50% or more of any liquid carrier and more preferably warmed to the extent to evaporate substantially all the compound liquid carrier leaving the particles dry, i.e. leaving the particles in a form where any liquid carrier such as water and/or ethanol which is not complexed with or bound to the drug has been evaporated away. The device is a hand-held, self-contained device which has a total weight of 1 kilogram or less in its loaded form.

The aerosol generation device to be combined with the present invention is preferably loaded with a disposable drug container of the type disclosed within U.S. Pat. No. 5,497,763 issued Mar. 12, 1996—see also U.S. Pat. No. 5,544,646 issued Aug. 13, 1996, U.S. Pat. No. 5,660,166 issued Aug. 26, 1997, and U.S. Pat. No. 5,718,222 issued Feb. 17, 1998, all of which are incorporated herein by reference to disclose a aerosol generation device and a disposable container for containing a drug for aerosolized delivery.

Different embodiments of the air temperature controlling device of the present invention may contain a variety of different power sources provided the power source is self-contained allowing the device to be hand held and portable. The power source may be a container of a liquid such as butane or propane, or is more preferably in the form of an electric cell or a plurality of electric cells, i.e. a battery. Typically, the receptacle holds a battery securely in place and has electrical metal contacts to contact a positive and negative end of an electric cell or battery. Different types of batteries can be used including rechargeable batteries. It is preferable to use standard size cells, more preferably AA (or similar) size cells. Specifically, the present invention has been developed so that it is very light weight and portable and can provide the necessary warming by power received from a few AA size electric cells. However, the invention is intended to encompass portable devices which include somewhat larger electric cells, e.g. D size electric cells or smaller.

The power source is brought into contact with electrical contacts on the receptacle thereby powering the drug delivery device. The electrical contacts of the receptacle lead to the heating element which is the most important aspect of the present invention and to other components of the device which require power.

The utility of the invention can be heightened by improving the efficiency of the air temperature controlling device, thus minimizing the number of batteries (and thus the size and weight of the drug delivery device), and maximizing the number of doses delivered before the power source needs to be replaced or recharged. The efficiency of the air temperature controller can be increased by insulating the walls of the air path, thus minimizing the amount of heat lost during the preheat and storage phases of the cycle. Additionally, a valving means can be used to only deliver conditioned air during the period of aerosol generation, and deliver ambient air during the parts of an inhalation prior to and following aerosol generation, thus minimizing the amount of preheating of the heating element required, and saving heat in the heating element for subsequent inhalations.

The heating element may take a variety of different forms but is preferably in the form of a coiled wire and most preferably in the form of a nickel chromium wire which is about 16 to 36 gauge and most preferably 26 gauge. Alternatively, the heating element may be formed of stamped metal of similar composition. The composition and physical structure of the heating element must be carefully designed in order to provide a heating element which can quickly store energy in the form of heat and thereafter quickly release that stored heat energy to the surrounding air. In addition, the heating element must be such that it can perform the heat storage and release tasks when being powered by a small power source such as a few AA electric cells.

The heating element must be designed so as to provide energy in the range of about 150 to 350 joules, most preferably about 250 joules to the surrounding air in a relatively short period of time, i.e. about 0.5 to 4.0 seconds, more preferably 1–2 seconds. In order to produce such a heating element and power source wherein the device remains small and portable it has been found that it is not possible to design the system wherein the energy is provided in real time (i.e. at the same time as the aerosol is generated) from an electrical power source, due to the internal impedance of existing battery technologies. Accordingly, the power source is used to preheat the heating element which acts as a heat sink before the energy is delivered. Thus, the concept is similar to the concept of charging a capacitor in order to operate a flash on a camera. In the same manner the heat sink or heating element of the invention acts as a "heat capacitor" and stores energy from the power source until sufficient energy is stored and then delivers that stored energy to the surrounding air at a rate well beyond that which would be possible with the power source itself. Alternatively, the power may be stored in an electrical capacitor, and then delivered to the heating element from the capacitor during aerosol generation. State of the art of high capacity, high discharge rate capacitors should be used. When the patient inhales through the device air is drawn over the heating element and energy is transferred to the air, warming the air. The precise amount of air warmed and the amount which the air is warmed to can be changed using different components in the temperature controlling device, or by changing the amount of preheating of the heating element prior to aerosol generation.

Optimum performance can be achieved by limiting the density of the aerosol generated. For example, it is typical to aerosolize a volume of formulation in the range of about 1 microliter to about 100 microliters per liter of inhaled air. By making the formulation more concentrated less energy is required per mass of drug delivered in order to evaporate away the carrier and produce smaller particles. However, when the formulation is more dilute the heat energy added can have a greater effect on reducing particle size. More specifically, since the more dilute solution will contain a larger amount of carrier the heating element can have a larger effect on reducing the particle size.

The invention preferably includes a control circuit to measure and control the temperature of the heating element. This is required to optimize the amount of preheating when, for example, the batteries are near the end of there useful lifetime. It could also monitor the temperature and relative humidity of the ambient air, and vary the amount of preheating accordingly. The control circuit may be an analog circuit, digital circuit, or hybrid analog/digital circuit, and preferably includes a microprocessor. The control circuit of the invention can be designed to add the desired amount of heat depending on the amount of carrier in the aerosol particles and (1) the density (number of aerosol particles per liter of air) of the generated aerosol (2) the size of the particles initially as well as (3) the size of the particles desired after the carrier has been evaporated away. The control of the aerosol generation device may be integrated in the same circuit, and may, for example, share the microprocessor which microprocessor may be the type disclosed in U.S. Pat. Nos. 5,404,871, 5,542,410 and 5,655,516.

The device may include a hygrometer for measuring ambient humidity and/or a temperature sensor for measuring ambient temperature. Information collected by the hygrometer and/or temperature sensor is supplied to the control circuit which determines the amount of energy to be added to the surrounding air by the heating element. As the humidity increases additional energy may be necessary in order to evaporate carrier away from the particles. In the preferred embodiment, the heating element warms the air sufficiently to evaporate essentially all of the carrier over the range of ambient conditions expected in the lifetime of the device, thus obviating the need for relative humidity/ambient temperature sensor.

In general, when the heating element is in the form of a 26 gauge nickel chromium wire the heating element has a weight of approximately 3 to 7 grams, more preferably 5 grams. The heating element preferably is capable of generating energy in an amount of about 20 joules or more, and generally generates energy in the amount of about 20 to 10 joules per 10 microliters of formulation.

It is pointed out that the device of the present invention can be used to, and actually does, improve the efficiency of drug delivery. However, this is a secondary feature. The primary feature is the improved reproducibility of the emitted dose and particle size over the range of ambient conditions likely to be encountered while using the device. The air temperature controlling device aids in improving repeatability by keeping the delivered aerosol particles inside of a closely controlled diameter range.

The methodology of the invention may be carried out using a portable, hand-held, battery-powered device using a microprocessor as disclosed in U.S. Pat. No. 5,404,871, issued Apr. 11, 1995 and U.S. Pat. No. 5,450,336, issued Sep. 12, 1995 incorporated herein by reference. The control circuit can be additionally designed to monitor inhalation flow rate, total inhaled volume, and other parameters, and commence generation of aerosol at a predefined optimal point during the inhalation. In accordance with the system the drug is included in an aqueous formulation which is aerosolized by moving the formulation through a porous membrane. The pre-programmed information is contained within nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these embodiments, changing the programming of the memory device readable by a microprocessor will change the behavior of the device by causing the microprocessor to be programmed in a different manner. This is done to accommodate different drugs for different types of treatment.

The drug which is released to the patient may be in a variety of different forms. For example, the drug may be an aqueous solution of drug, i.e., drug dissolved in water and formed into small particles to create an aerosol which is delivered to the patient. Alternatively, liquid suspensions or dry powders may be used. Alternatively, the drug may be in a solution wherein a low-boiling point propellant is used as a solvent.

Some peptide drugs are subject to being degraded more quickly when in solution such as an aqueous solution. Preferably such drugs are packaged in a dry form and mixed with water prior to administration. A dual compartment container for carrying out such is shown in U.S. Pat. No. 5,672,581. Alternately, the drug is kept in the form of a dry powder which is intermixed with an airflow in order to provide for delivery of drug to the patient.

Regardless of the type of drug or the form of the drug formulation, it is preferable to create aerosol particles having a size in the range of about 1 to 3.5 microns. By creating particles which have a relatively narrow range of size, it is possible to further increase the efficiency of the drug delivery system and improve the repeatability of the dosing. Thus, it is preferable that the particles not only have a size in the range of 1.0 to 3.5 microns but that the mean particle size be within a narrow range so that 80% or more of the particles being delivered to a patient have a particle diameter which is within ±50% of the average particle size, preferably ±25% of the average particle size. The heating element is particularly useful in reducing particle size and in creating a aerosol with uniform sized particles.

The amount of drug delivered to the patient will vary greatly depending on the particular drug being delivered. In accordance with the present invention it is possible to deliver a wide range of drugs. For example, drugs delivered could be drugs which have a systemic effect e.g. leuprolide, insulin and analogs thereof including monomeric insulin, or morphine; or a local effect in the lungs e.g. Activase, albuterol, or sodium cromoglycate.

TABLE 3

Useful Peptide Hormone Drugs

| Compound | Amino acids |
| --- | --- |
| Somatostatin | 6 |
| Oxytocin | 9 |
| Desmopressin | 9 |
| LHRH | 10 |
| Nafarelin | 10 |
| Leuprolide | 11 |
| ACTH analog | 17 |
| Secretin | 27 |
| Glucagon | 29 |
| Calcitonin | 32 |
| GHRH | 40 |
| Growth hormone | 191 |

Having generally described the invention above reference is now made to the figures in order to more particularly point out and describe the invention.

FIG. 1 is a graph of deposition fraction versus particle diameter with the particle diameter being the aerodynamic diameter of a particle having a density of 1 gram per square centimeter with the scale being read in terms of increasing particle diameter in units of μm. The aerodynamic diameters are plotted versus the deposition fraction in the lungs. For each of the different lines shown on the graph the data is provided for the deposition fraction in the different areas of the lung and for the total deposition. As can be seen on the graph the oro-pharyngeal deposition which is basically in the back of the throat occurs for particles which are somewhat large. Specifically, as the particle size increases to an aerodynamic diameter above 10 μm nearly all of the particles are deposited in the oro-pharyngeal area. It is pointed out that the graph does not represent actual data but is believed to be a fairly accurate representation of what occurs during intrapulmonary drug delivery particularly where the patient being tested is breathing at a rate of 15 breaths per minute with a 750 ml tidle volume.

Figure 2:
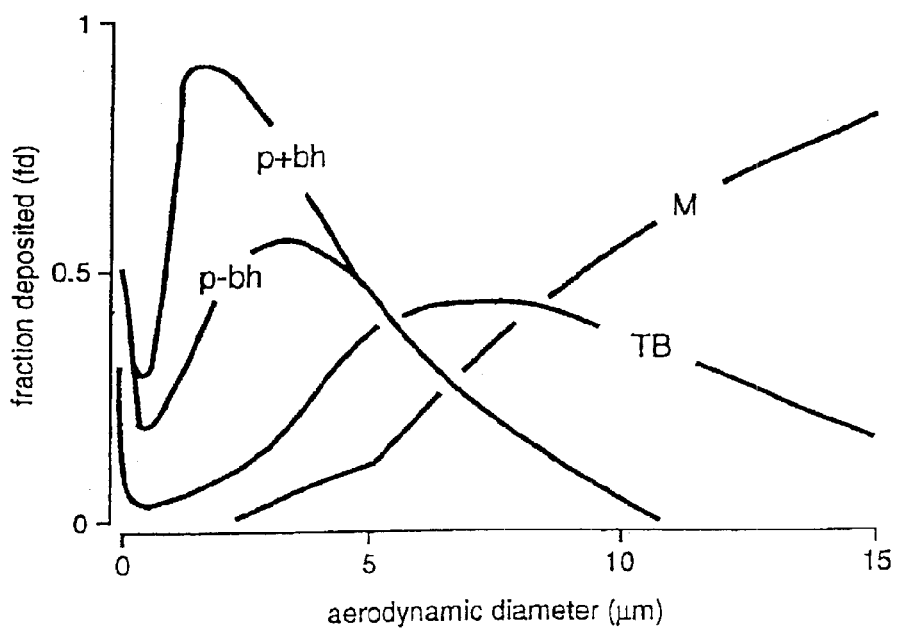
FIG. 2 is a graphic model similar to FIG. 1, showing the effect of a breath hold maneuver on lung deposition.

FIG. 2 is similar to FIG. 1 and is a plot of aerodynamic diameter versus fractional deposition. In FIG. 2 the graphs show "p" which is pulmonary deposition with "bh" breath holding and without breath holding. Similar to FIG. 1, this graph represents theoretical and not actual data. As can be seen in the graph the breath holding technique does improve the amount of pulmonary deposition. Particularly when the particles have an aerodynamic diameter less than 5 μm.

FIGS. 1 and 2 together clearly indicate the importance of the present invention. Specifically, the figures indicate that the area of the lung which particles deposit in and the percentage of the particles which deposit there is substantially effected by the aerodynamic diameter of the particles. In that the present invention makes it possible to provide for consistent aerodynamic particle size the invention provides for consistent delivery of the particles to particular areas of the lung and therefore repeatable dosing of a patient.

Figure 3:
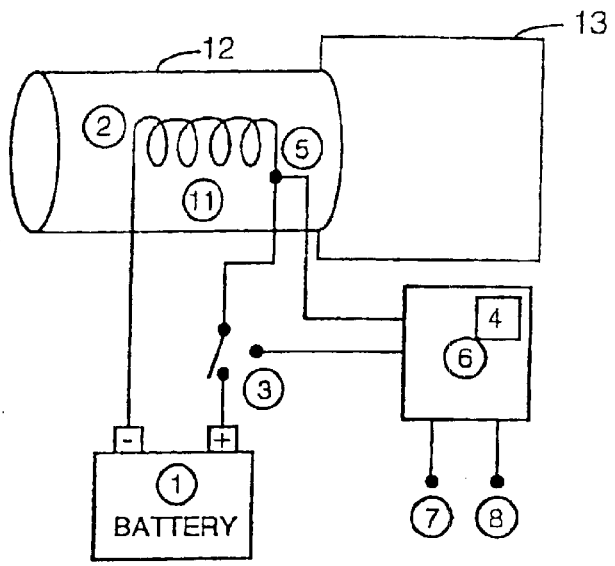
FIG. 3 is a schematic view of an embodiment of a air temperature controlling device of the invention.

FIG. 3 schematically shows an embodiment of the air temperature controller. Battery 1 is electrically connected to heating element 2 through relay 3. The relay 3 may be a mechanical, or preferably a solid state relay. Relay 3 is controlled by control circuit 6 which includes microprocessor 4. Temperature sensor 5 is in thermal contact with heating element 2, and is monitored by control circuit 6. Optional ambient relative humidity sensor 7 and ambient temperature sensor 8 are also monitored by control circuit 6. Ready light 9 (see FIG. 4) is controlled by microprocessor 4. Power for the entire system is supplied by battery 1. The heating element 2 is positioned in air path 11 formed by the cylinder 12, leading to aerosol generation device 13.

Figure 4:
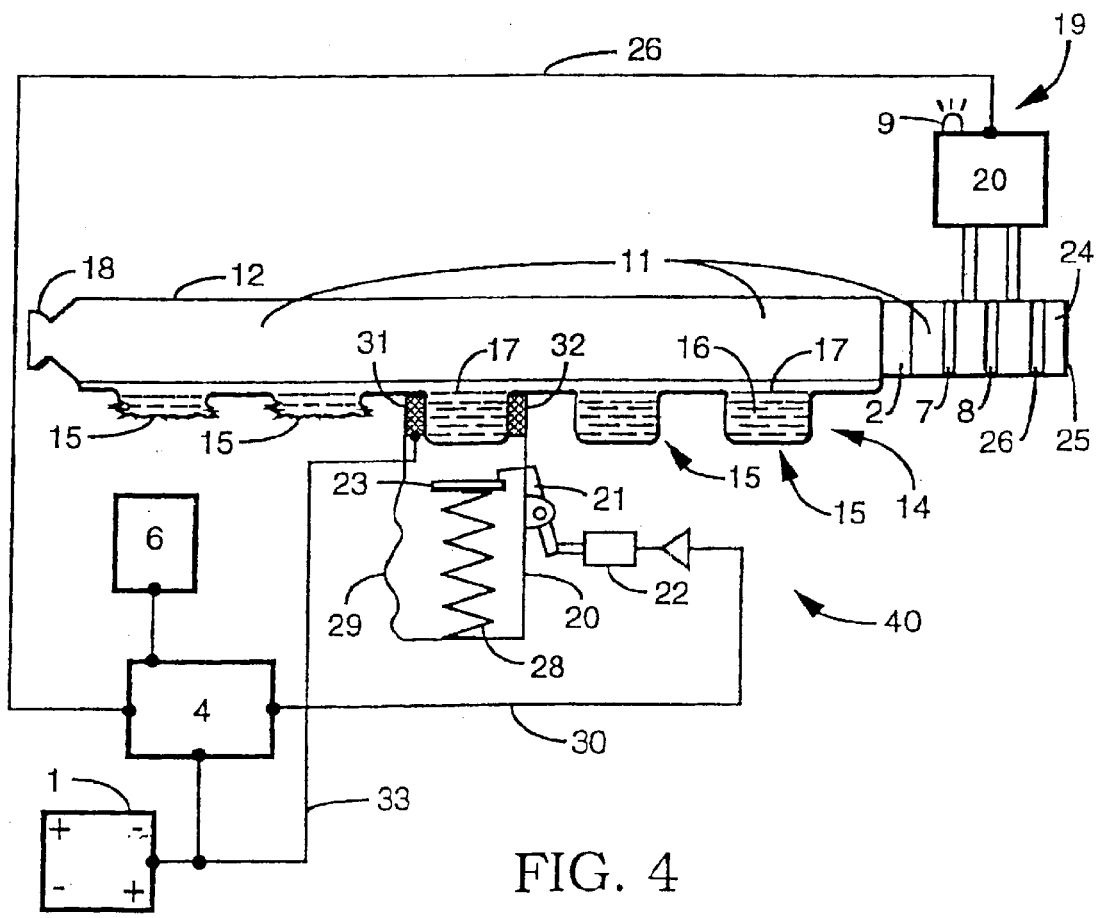
FIG. 4 is a schematic view of an embodiment of an aerosol delivery device of the invention.

FIG. 4 is an embodiment of an aerosol drug delivery device utilizing the invention. The device 40 shown in FIG. 4 is loaded with a disposable package 14. To use the device 40 a patient inhales air from the mouthpiece 18 through the opening 25 in the cylinder 12. The air drawn in through the opening 25 (and optionally the desiccator 24) flows through the flow path 11 of the channel 12. The disposable package 14 is comprised of a plurality of disposable containers 15. Each container 15 includes a drug formulation 16 and is covered by a nozzle array or porous membrane 17. The heating element 2 is located in the flow path 11. The heating element 2 is preferably positioned such that all or only a portion of the air flowing through the path 11 will pass by the heating element 2, e.g., flow vent flaps can direct any desired portion of air past the heating element 2. The relay 3 (see FIG. 3) is preferably closed for 30 sec or less prior to inhalation and opened after drug delivery to conserve power.

The device 40 may include a mouth piece 18 at the end of the flow path 11. The patient inhales from the mouth piece 18 which causes an inspiratory flow to be measured by flow sensor 19 within the flow path which path may be, and preferably is, in a non-linear flow pressure relationship. This inspiratory flow causes an air flow transducer 20 to generate a signal. This signal is conveyed to a microprocessor 4 which is able to convert the signal from the transducer 20 in the inspiratory flow path 11 to a flow rate in liters per minute. The microprocessor 4 can further integrate this continuous air flow rate signal into a representation of cumulative inspiratory volume.

When the device is turned on by the user, the microprocessor 4 will send a signal to send power from the power source 1 (which is preferably a small battery) to the air temperature controller 2 and will continue to preheat the temperature controller 2 until it reaches a predetermined temperature. The preheat temperature can be preprogrammed based on such information as the particle size generated, the particle size desired, the formulation concentration, and other parameters. The microprocessor 4 may also adjust the preheat temperature to optimize each delivery based on the ambient conditions, using information from the optional hygrometer/temperature sensor 7. The microprocessor 4 also sends a signal to an actuator 22 which causes the mechanical means (e.g., the piston 23) to force drug from a container 15 of the package 14 into the inspiratory flow path 11 of the device 40 where the aerosol is formed and entrained into the inhalation air and delivered into the patient's lungs.

When the formulation 16 includes water as all or part of the carrier it may also be desirable to include a desiccator 24 within the flow path 11. The desiccator 24 is preferably located at the initial opening 25 but maybe located elsewhere in the flow path 11 prior to a point in the flow path when the formulation is fired into the flow path in the form of aerosol particles. By drawing air through the desiccator 24 water vapor within the air is removed in part or completely. Therefore, only dried air is drawn into the remainder of a flow path. Since the air is completely dried, water carrier within the aerosol particles will more readily evaporate. This decreases the energy needs with respect to the temperature controller 2. The desiccator material can be any compound which absorbs water vapor from air. For example, it may be a compound selected from the group consisting of $P_2O_5$, $Mg(ClO_4)$, KOH, $H_2SO_4$, NaOH, CaO, $CaCl_2$, $ZnCl_2$, and $CaSO_4$.

Device Operation

The operation of the device 40 can be understood by reference to a combination of FIGS. 3 and 4. Referring to FIG. 3 when the relay 3 is closed the heating element 2 begins to heat. In addition to the heating element 2 present within the flow path 11 the flow path may also include a humidity sensor 7, temperature sensor 8 and electronic airflow sensor 26. When a patient (not shown) inhales through the mouth piece 18 air flows in through the opening 25 and is sensed by the air flow sensor 26 after being electronically converted by the transducer 20. The signal flows along the electrical connection 26 to the microprocessor 4. The combination of the control circuit 6 and the microprocessor 4 send a signal back through the connection 26 to the heating element 2 which is powered by the battery 1. The amount of power to be supplied to the heating element 2 is also tempered, to a degree, by information received from the humidity sensor 7 and temperature sensor 8 which information is considered by the microprocessor 4. When the heating element 2 reaches the correct temperature and the air flow sensor 26 determines that the inspiratory flow rate and inspiratory volume are at the desired point the microprocessor 4 sends a signal to the actuator 22. The actuator 22 may be any type of device such as a selenoid which then moves the mechanical release member 21 so that the piston 23 is released. The piston 23 is forced upward by a spring or other biasing means 28. The biasing means may be held within a grip 29 which can be easily held by the user. Where the microprocessor 4 sends the signal through the line 30 to the actuator 22 the spring is released and a container 15 is crushed and the formulation 16 inside the container is released through the membrane 17.

When the container 15 is present in the drug release position below the piston 23 the container 15 may have vibrating devices 31 and 32 positioned on either side or a single device surrounding the container 15. The vibrating device(s) may be actuated by the microprocessor 4 sending a signal through the connection 23. Empty containers 15 are shown to the left of the drug actuation point. In a preferred embodiment of the methodology a new container and new porous membrane are used for each drug release. By using a new porous membrane each time clogging of the porous membranes is avoided. Further, possible contamination of the formulation 16 present in the container 15 is avoided.

Those skilled in the art will recognize that a variety of different components could be used in place of some of the components shown within FIGS. 3 and 4. For example, rather than including a piston biased by a spring it would be possible to utilize a rotating cam. Further, other components of the invention, although preferred, are not required. For example, components such as the humidity sensor 7 and temperature sensor 8 could be eliminated without substantial impairment of operability by simply adjusting the amount of energy supplied to the heating element 2 so as to compensate for any humidity or temperature which might be encounter by the user. However, such would acquire the use of unnecessary amounts of power in some situations.

When the air temperature controller shown in FIG. 3 is activated, microprocessor 4 closes relay 3, commencing the preheat of heating element 2. Microprocessor 4 monitors temperature sensor 5 until heating element 2 reaches a temperature that is determined by ambient conditions as measured by optional ambient relative humidity sensor 7 and/or ambient temperature sensor 8, or preferably a temperature that has been previously determined to be sufficient for all ambient conditions to be seen in the normal operation of the device. When this temperature is reached, the microprocessor opens relay 3 to inhibit further heating, and lights the ready light 9 to signal to the patient that the device is ready for a dosing event. The microprocessor continues to monitor temperature sensor 7 and opens and closes relay 3 as required to maintain the desired temperature until the patient inhales from the device.

Energy for Evaporation

Figure 5:
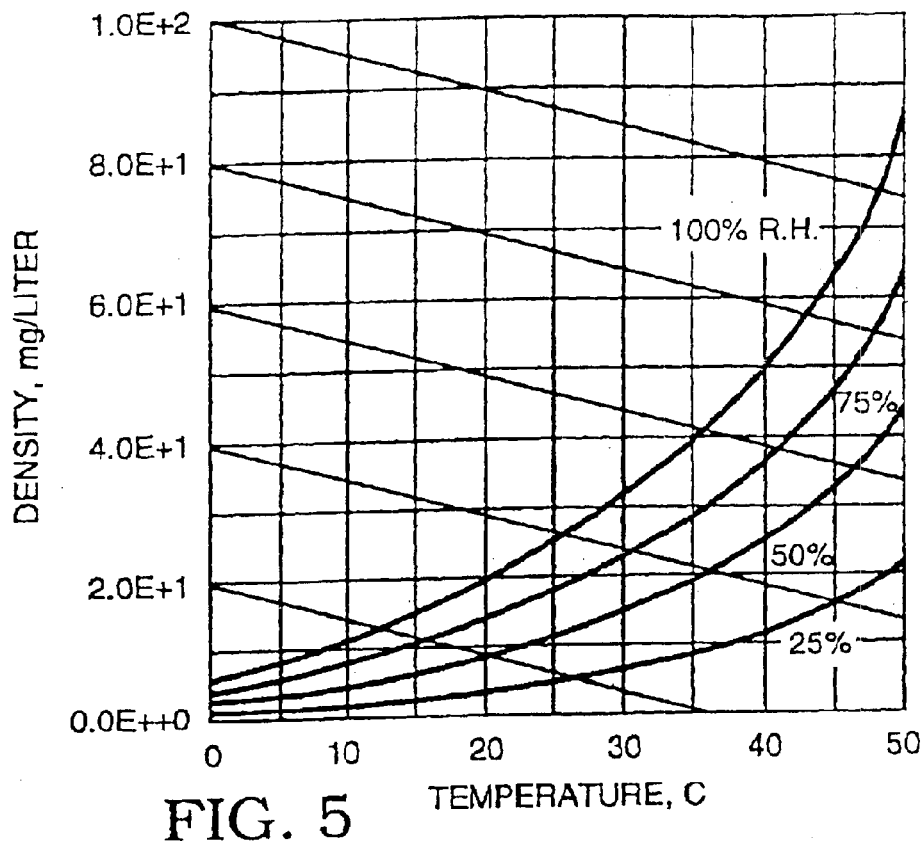
FIG. 5 is a graph plotting the density (mg/liter) of water vapor in air versus temperature.

FIG. 5 is a graph which can be used in calculating the amount of energy needed to control the size of delivered droplets by controlling the amount of evaporation of carrier from the aerosolized droplets. The graph of FIG. 5 contains two types of information, the density of evaporated water vs. temperature and relative humidity, and the cooling of the air as the water evaporates. The four lines that show a rapid increase with temperature portray the density of water vapor in air, at 25, 50, 75, and 100% relative humidity. The 100% relative humidity curve represents the maximum number of milligrams of water that can be evaporated per liter of air. The diagonal lines show the temperature change of the air as the water droplets evaporate (hereafter called the air mass trajectory curves). As the evaporation proceeds, the density and temperature will change by moving parallel to these curves. To calculate these curves, air density of 1.185 grams/liter, air specific heat of 0.2401 calories/gram, and water latent heat of vaporization of 0.583 cal/mg were assumed. It is also assumed that the evaporation process is adiabatic, i.e. there is no heat removed from or supplied to the air from other sources such as the walls of the device. These values imply that a liter of air will cool 2 degrees Celsius for every milligram of water evaporated, i.e. evaporating 10 micro-liters will cool a liter of air 20 degrees Celsius.

FIG. 5 can be used to calculate the amount of preheating needed to evaporate all or substantially all of the carrier in the aerosol particles. As an example, assume the initial ambient conditions are 25° C. and 50% relative humidity. Further, assume that one wants to evaporate 10 $\mu$l (10 mgs) of water from an aqueous drug solution. Finally, assume the final relative humidity is 75%. Under these conditions the aqueous carrier would not in general evaporate completely. More specifically, the final particles would contain approximately equal amounts of drug and water. To calculate the amount of energy to add for this delivery maneuver, refer to FIG. 5. Locate the point corresponding to 25° C. and 50% relative humidity. Move up by 10 milligrams, the amount of water to be evaporated. Now move to the left until the 75% RH curve is crossed. This occurs at about 29° C. These conditions (75% RH and 29° C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47° C. Thus, sufficient heat to warm the air by 22° C. must be added to achieve near complete evaporation.

Figure 6:
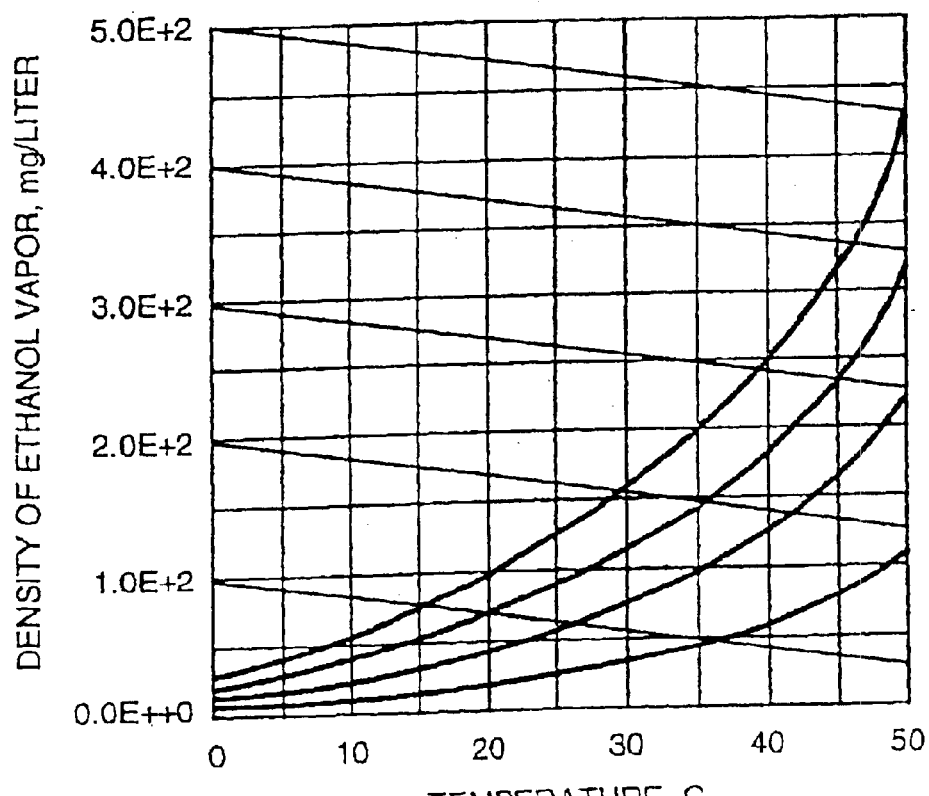
FIG. 6 is a graph plotting the density (mg/liter) of ethanol vapor in air versus temperature.

FIG. 6 includes similar information with respect to ethanol which can be used in a similar manner. A preferred embodiment of the invention comprises a microprocessor programmed to calculate the amount of energy needed for the formulation being aerosolized with consideration to the surrounding temperature and humidity being accounted for. In a preferred embodiment, containers of formulation loaded into the device are labeled in a manner which is read by the device which then considers the size of the formulation dose to be aerosolized and the amount of liquid to be evaporated.

The evaporation and growth rates of aqueous droplets is a function of their initial diameter, the amount of drug dissolved therein (concentration) and the ambient relative humidity and temperature. The determining factor is whether the water vapor concentration at the surface of the droplet is higher or lower than that of the surrounding air. Because the relative humidity at the surface of a particle (i.e. droplet of aerosolized formulation) is close to 100% for most formulations of interest, evaporation will occur under most ambient conditions until the rising humidity of the air equals the decreasing humidity at the surface of the droplet. A five micron droplet will evaporate to a 1 micron dry particle in 0% humidity in less than 20 ms.

When administering drug using the inhalation device of the present invention, the entire dosing event can involve the administration of anywhere from 10 μl to 1,000 ml of drug formulation, but more preferably involves the administration of approximately 30 μl to 200 μl of drug formulation. Very small amounts of drug (e.g., nanogram or larger amounts) may be dissolved or dispersed within a pharmaceutically acceptable, liquid, excipient material to provide a liquid, flowable formulation which can be readily aerosolized. The container will include the formulation having drug therein in an amount of about 10 μg to 300 mg, more preferably about 1 mg. The large variation in the amounts which might be delivered are due to different drug potencies and different delivery efficiencies for different devices, formulations and patients.

System Specification Envelope

The following information is provided to specify an approximate envelope for the design of the temperature controlling system.

A. Batteries
  Chemistry: Nickel Cadmium, Nickel Metal-Hydride, Lithium-Ion, Lithium-Metal,
  Lithium Polymer
  Voltage: 1 Volt to 20 Volt
  Internal, Impedance: less than 0.1Ω per cell
  Number of cells: 1 to 10
B. Heating Element
  Total Heat Capacity: 0.2 J/C to 4.35 J/C
  Surface Area: 10 $cm^2$ to 150 $cm^2$
  Electrical Resistance: 0.5Ω to 5Ω
  Mass: 1–10 grams
C. Control Relay
  Type: Solid State, Mechanical, Transistor
D. Temperature Sensors
  Types: Resistance, Thermocouple, Diode

EXAMPLES

The following examples are put forth so as to provide those of ordinary skill in the art with a complete disclosure and description of how to make and use various constructs and perform the various methods of the present invention and are not intended to limit the scope of what the inventors regard as their invention nor are they intended to represent or imply that the embodiments described below are all on the only embodiments constructed or tested. Efforts have been made to ensure accuracy with respect to numbers used (e.g., amounts, concentrations, particular components, etc.) But some deviations should be accounted for.

Example 1

Figure 7:
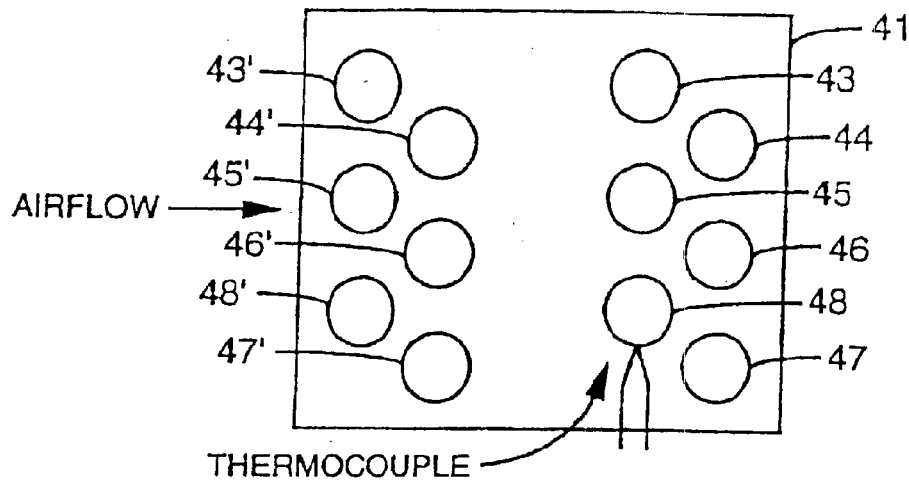
FIG. 7 is an overhead schematic view of the temperature controlling apparatus.
Figure 8:
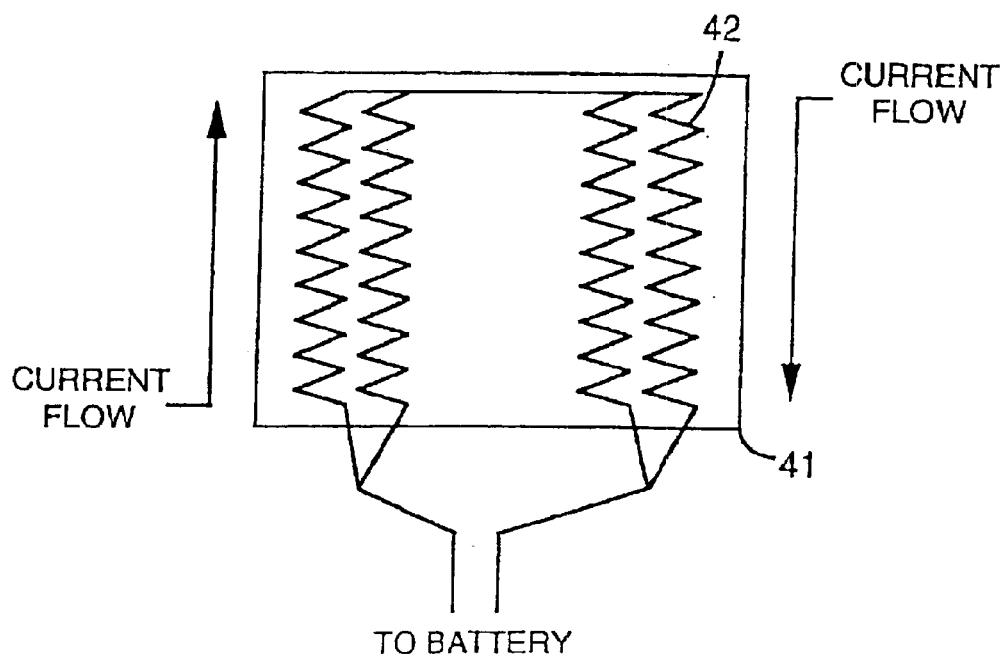
FIG. 8 is a side schematic view of the temperature controlling apparatus.

A preferred embodiment of a temperature controller system 41 is shown in FIGS. 7 and 8. The system is comprised of wire 42 of total length of 130 inches. The 2.2 gram wire is split into six coils 43, 44, 45, 46, 47 and 48, each having approximately 8.4Ω resistance. Each 8.4Ω coil is then split in half forming coils 43', 44', 45, 46', 47' and 48', making a total of 12 coils. The twelve coils are then split into two banks of six coils each that are staggered as shown in FIG. 7 which depicts their arrangement. Current flow is shown in FIG. 8 with air flow shown in FIG. 7.

The heating element is placed inside a flow channel (11 shown in FIG. 4) (dimensions 3 cm×2 cm×1.5 cm) that is open at one end to the air, and the other end open to the aerosol generation device. The total electrical resistance of the temperature controller is ~1.6Ω (1.4Ω for heating element coils and ~0.2Ω for various electrical connections). A thermocouple is soldered onto one of the coils to monitor the temperature. The coils are heated until they reach a pre-specified temperature and then maintained at that temperature until activation of the aerosol generation device.

To power the system, ten AA-sized Nickel Metal-Hydride cells (or less, e.g., four, six, seven or eight) are connected in series to give a battery voltage of 18 7.2 V. The cells each have a capacity of 1.3 Ahr.

Example 2

In another embodiment (not shown in the figures) the heating element is a 24 gauge wire of a nickel-copper alloy, wound in a conical coil or series of coils. The axis of the cone lies along the center of the air flow path. The temperature of the coil is monitored by a platinum RTD, which is attached to the heating element. The heating element consists of wire of total length of 80 inches. The 3.6 grams of wire is split into four conical coils, each having approximately 0.35Ω resistance. The four coils are wired in series, for a total resistance of 1.4 Ω.

The heating element is placed inside a cylindrical flow channel (dimensions 0.875" diameter, 1.5" long) that is open at one end to the air, and the other end open to the aerosol generation device.

To power the system, ten or less (particularly seven) AA-sized Nickel cadmium cells are connected in series to give a battery voltage of ~8.4 V. The cells each have a capacity of 1.3 Ahr.

The invention as shown and described is considered to be the one of the most practical and preferred embodiments. It is recognized, however, that the departures may be made therefrom which are within the scope of the invention and that obvious modifications will occur to one skilled in the art upon reading this disclosure.

What is claimed is:

1. A method, comprising:
   aerosolizing a liquid formulation comprised of a pharmaceutically active drug;
   supplying the current from a battery having a physical sign equivalent to or smaller than two standard D size electric cells;
   heating the aerosol by application of the current from the battery to a wire coil comprising copper and a metal chosen from chromium and iron, the wire having a total heat capacity of about 0.2 to 4.35 J/° C. and a gauge in a range of from about 16 to about 36 and weighting from about 0.5 gram to about 10 grams and having a surface area of about 10 $cm^2$.

2. The method of claim 1, further comprising:
   drawing the aerosol through a channel comprising an air flow path and an opening into which air is inhaled.

3. The method of claim 2, further comprising:

sensing ambient conditions and adjusting current supplied based on sensed ambient conditions.

4. A drug delivery device, comprising:

a channel comprising an air flow path, a first opening into which air can be inhaled and a second opening comprising a mouthpiece from air can be drawn;

a heating element comprising a wire coil with a total heat capacity of about 0.2 to 4.35 J/° C. and having a mass of about 0.5 gram to about 10 grams and a surface area of about 10cm$^2$ to about 150 cm$^2$, and a resistance in a range of from about 0.5 ohm to about 5 ohms the heating element positioned in the flow path of the channel.

5. The device of claim 4, wherein the heating element has a mass of about 2 to 4 grams.

6. The device of claim 4, further comprising:

a portable source of power capable of supplying sufficient power to the heating element, over a period of less than or equal to one minute to enable the heating element to deliver about 150 to 350 Watts of energy to surrounding air in about 0.5 to 4.0 seconds.

7. The device of claim 6, where the portable power source comprises a battery capable of supplying a voltage within the range of about 1 to 20 Volts.

8. The device of claim 4, wherein the heating element is configured to deliver about 150 to 350 Watts of energy to surrounding air in about 0.5 to 4.0 seconds.

9. The device of claim 8, wherein the heating element is configured to deliver about 250 Watts of energy to surrounding air in about 1 to 2 seconds.

10. The device of claim 4, wherein the heating element comprises nickel chromium wire and has a mass of about 3 to 7 grams.

11. The device of claim 10, wherein the heating element has a mass about 5 grams.

12. The device of claim 4, wherein the heating element is capable of generating at least 20 joules of heat energy when connected with a portable power source over a period of less than or equal to one minute.

* * * * *